(12) United States Patent
Ogawa

(10) Patent No.: US 12,402,854 B2
(45) Date of Patent: Sep. 2, 2025

(54) MEDICAL DEVICE AND PROGRAM

(71) Applicant: AMI INC., Kumamoto (JP)

(72) Inventor: Shinpei Ogawa, Kumamoto (JP)

(73) Assignee: AMI Inc., Kumamoto (JP)

( * ) Notice: Subject to any disclaimer, the term of this patent is extended or adjusted under 35 U.S.C. 154(b) by 737 days.

(21) Appl. No.: 17/637,820

(22) PCT Filed: Sep. 18, 2020

(86) PCT No.: PCT/JP2020/035489
§ 371 (c)(1),
(2) Date: Feb. 24, 2022

(87) PCT Pub. No.: WO2021/054446
PCT Pub. Date: Mar. 25, 2021

(65) Prior Publication Data
US 2022/0280132 A1 Sep. 8, 2022

(30) Foreign Application Priority Data
Sep. 20, 2019 (JP) .................................. 2019-172335

(51) Int. Cl.
*A61B 7/04* (2006.01)
*A61B 5/02* (2006.01)

(52) U.S. Cl.
CPC . *A61B 7/04* (2013.01); *A61B 5/02* (2013.01)

(58) Field of Classification Search
None
See application file for complete search history.

(56) References Cited

U.S. PATENT DOCUMENTS 6,869,404 B2 * 3/2005 Schulhauser ........ A61B 5/0215
600/528
7,130,429 B1 * 10/2006 Dalgaard ................. A61B 7/04
381/67

(Continued)

FOREIGN PATENT DOCUMENTS

JP         2009-240527 A    10/2009
JP    WO2013/089073 A1     6/2013

(Continued)

OTHER PUBLICATIONS

International Search Report of International Patent Application No. PCT/JP2020/035489 completed Oct. 14, 2020 and mailed Oct. 27, 2020 (5 pages).

(Continued)

*Primary Examiner* — Shirley X Jian
(74) *Attorney, Agent, or Firm* — Pyprus Pte Ltd; George D. Liu

(57) ABSTRACT

[Problem] To provide a medical device which can acquire measurement results with high reproducibility even when a stethoscope vibration receiver is placed against the part being inspected with an inconstant strength or position. [Solution] This medical device (100) is provided with a vibration receiver (20) which can record heart sounds in a frequency region that includes frequencies less than 20 Hz, and a frequency analyzer (11) which identifies the frequency in said frequency band at which the power is greatest. By adopting a vibration receiver (20) which can record heart sounds in a frequency band that includes frequencies less than 20 Hz and by identifying the frequency in said frequency band that has the greatest power, measurement results are less prone to being affected by the operation environment of the stethoscope vibration receiver.

9 Claims, 5 Drawing Sheets

(56) References Cited

U.S. PATENT DOCUMENTS

| | | | |
|---|---|---|---|
| 10,111,643 B2 * | 10/2018 | Schulhauser | A61B 5/352 |
| 10,420,527 B2 * | 9/2019 | Misra | A61B 7/00 |
| 10,441,181 B1 * | 10/2019 | Telfort | A61B 5/02455 |
| 2004/0167417 A1 * | 8/2004 | Schulhauser | A61B 5/0006 |
| | | | 600/513 |
| 2004/0260188 A1 * | 12/2004 | Syed | A61B 7/04 |
| | | | 600/509 |
| 2006/0079782 A1 * | 4/2006 | Beach | G01S 7/52034 |
| | | | 600/450 |
| 2011/0257548 A1 * | 10/2011 | Dong | A61B 7/04 |
| | | | 600/528 |
| 2016/0302732 A1 * | 10/2016 | Misra | A61B 7/00 |
| 2017/0265838 A1 * | 9/2017 | Schulhauser | A61B 5/746 |
| 2018/0043158 A1 * | 2/2018 | Thakur | A61B 5/02438 |
| 2020/0245889 A1 * | 8/2020 | Telenkov | A61B 5/6885 |
| 2023/0414192 A1 * | 12/2023 | Masuda | A61B 5/02 |

FOREIGN PATENT DOCUMENTS

| | | |
|---|---|---|
| JP | 2014-87543 A | 5/2014 |
| JP | 2014-90916 A | 5/2014 |
| JP | 2015-188511 A | 11/2015 |
| JP | WO2015/170772 A2 | 11/2015 |
| JP | 2017-538454 A | 12/2017 |

OTHER PUBLICATIONS

Written Opinion of International Patent Application No. PCT/JP2020/035489 completed Oct. 14, 2020 and mailed Oct. 27, 2020 (4 pages).

* cited by examiner

MEDICAL DEVICE AND PROGRAM

TECHNICAL FIELD

The present invention relates to a medical device and a computer program for analyzing a heart sound collected by a vibration receiver (for example, electronic stethoscope). Specifically, the present invention relates to a medical device and a computer program for analyzing a heart sound of a subject and diagnosing his/her cardiac function.

BACKGROUND ART

Recently, an electronic stethoscope configured to collect a heart sound of a subject, convert the heart sound into digital information, and analyze and record the digital information has become popular. Especially, because the use of the electronic stethoscope allows transmitting and receiving heart sound information via communications network such as Internet, the use of the electronic stethoscope is expected in remote medicine in which a doctor or another person engaged in medical treatment (hereinafter, collectively referred to as a "doctor") provides a medical service to a patient located in a remote area in real time.

Relating to the electronic stethoscope, Patent Document 1 discloses a technique in which criteria for classifying features of sound waveforms are applied to a sound waveform included in biological sound information (heart sound and the like) collected by a stethoscope, thereby identifying the feature of the sound waveform and determining the type of the sound to which the biological sound information belongs based on the feature of the sound waveform. According to this technique, the biological sound information can be objectively analyzed with accuracy, and the analysis result can be presented so as to be efficiently available for a user.

Patent Document 1: Pamphlet of WO2013/089073

DISCLOSURE OF THE INVENTION

Problems to be Solved by the Invention

Now, in the remote medicine, it is desired to easily receive the medical service while the subject (patient) stays at home, and in a situation of using the electronic stethoscope, it is assumed that the subject himself/herself or his/her caregiver applies the stethoscope to the chest of the subject for use. However, for example, when a process of analyzing the frequency of the heart sound collected by the electronic stethoscope and quantifying the amplitude power for each frequency, such an amplitude power generally varies influenced by a pressure of applying the stethoscope to the living body. That is, it was found by the study by the inventor that since the measurement result of the amplitude power was affected by the strength (pressure) of applying the stethoscope, the reproducibility was poor even for the same subject. Especially, when the subject or his/her caregiver is not a doctor or a person engaged in medical treatment, since the strength of applying the stethoscope to the chest significantly varies from time to time, the reproducibility of the measurement result of the amplitude power is significantly reduced.

Furthermore, it was also found by the study by the inventor that even when the heart sound was collected by applying the stethoscope to the same subject with the approximately same pressure, the measurement result of the amplitude power was differed only by a slight difference of the position at which the stethoscope is applied. It is inferred that this is because a distance from a site emitting the vibration (that is, heart) to the stethoscope and the frequency characteristic of a substance present between the site and the stethoscope are differed depending on the position at which the stethoscope is applied.

Therefore, the present invention has a main object to provide a medical device that allows obtaining a measurement result with high reproducibility even when a strength or a position of applying a vibration receiver (stethoscope and the like) to an examination site is not constant.

Solutions to the Problems

The inventor of the present invention earnestly examined a solution for the above-described problem of the prior art, and as a result, acquired a knowledge that, by employing one configured to collect heart sounds in a frequency band including less than 20 Hz as a vibration receiver and identifying a frequency with peak power in the frequency band, the measurement result is less likely to be affected by the operation environment of the vibration receiver. Then, the inventor thought that the problem of the prior art can be solved based on the above-described knowledge and completed the present invention. Specifically, the present invention has the following configuration.

The first aspect of the present invention relates to a medical device. The medical device according to the present invention includes a vibration receiver configured to collect heart sounds in a frequency band including less than 20 Hz, and a frequency analysis unit configured to identify a frequency with peak power in the frequency band. The vibration received by the vibration receiver includes a biological vibration and an air vibration (that is, a sound). The vibration receiver only needs to have 0 to 20 Hz as a lower limit value of the frequency band in which the sound can be collected. However, as illustrated in FIG. 2 (B1), the vibration receiver is preferably configured to detect the peak power of the heart sound in a low frequency band of 0 to 30 Hz, and furthermore, especially preferably configured to detect the power within −30 Hz relative to the peak power in the entire band of 0 to 20 Hz. The frequency analysis unit only needs to basically has a function of identifying the frequency with peak power (amplitude) in the frequency band obtained by the vibration receiver. Specifically, the frequency analysis unit may identify the frequency with peak power (amplitude) in all the frequency bands in one beat of the heart sound obtained by the vibration receiver, and may identify the frequency with peak power (amplitude) in the frequency band of a specific sound component (first heart sound, second heart sound, sound in rapid filling phase, and the like) constituting one beat of a heart sound. That is, the frequency with peak power may be identified in the entire time period of one beat of the heart sound, and the frequency with peak power may be identified among the sound components obtained by time-division of one beat of the heart sound.

As the above-described configuration, by employing the vibration receiver configured to appropriately obtain the frequency component of less than 20 Hz included in the heart sound and performing a process of identifying the frequency with peak power in the frequency band obtained by the vibration receiver, the measurement result with high reproducibility can be obtained even when a strength (pressure) and a position of applying the vibration receiver to an examination site are not constant. That is, while the biological sound, which is mainly the heart sound, includes various frequency components from the component close to 0 Hz (direct current) to the component exceeding 1000 Hz, it was found by the study by the inventor that, among the various frequency components, the component around 20 Hz in the biological vibration had the peak power. Additionally, it was found that the component around 20 Hz (especially, 0 to 30 Hz) was less likely to be affected by the operation environment of the vibration receiver, and for example, even when the strength and the position of applying the vibration receiver to an examination site were different, the maximum value of the amplitude power was less likely to change. Furthermore, the frequency value indicating the peak power is hardly affected by the strength and the position of applying the vibration receiver. Therefore, by using the vibration receiver configured to collect the sound of less than 20 Hz and identifying the peak power, the measurement result with high reproducibility can be obtained. Note that the conventional common electronic stethoscope does not have the performance of appropriately obtaining the components of less than 20 Hz included in the heart sound because of the characteristic of audible range of human having the lower limit of 20 Hz, and the peak power in the detectable frequency band is detected in the band of exceeding at least 30 Hz. Therefore, the conventional electronic stethoscope has a difficulty in obtaining the measurement result with high reproducibility as the medical device according to the present invention.

In the medical device according to the present invention, the frequency analysis unit preferably identifies the frequency with peak power in a low frequency band of 30 Hz or less. As described above, when the vibration receiver can appropriately obtain the frequency component of less than 20 Hz included in the heart sound, the frequency component with peak amplitude power usually appears in the low frequency band of 30 Hz or less. Therefore, the frequency analysis unit identifies the frequency with peak power in the low frequency band of 30 Hz or less. The frequency analysis unit may perform the process of identifying the frequency band with peak power from all the frequency bands obtained by the vibration receiver, and the peak power may appear in the low frequency band of 30 Hz or less. The frequency analysis unit may perform a process in which the analysis target of the power is limited to the low frequency band of 30 Hz or less and the frequency band with peak power is identified in the low frequency band. Thus, with the frequency analysis unit configured to identify the frequency with peak power in the low frequency band, the measurement result with high reproducibility can be obtained as described above.

In the medical device according to the present invention, the frequency analysis unit preferably traces changes over time of the frequency with peak power. By such tracing of the changes of the frequency with peak power of the heart sound, the medical device can be used for the diagnosis of the cardiac function of the subject.

The medical device according to the present invention preferably further includes a cardiac function diagnostic unit. The cardiac function diagnostic unit is preferably configured to identify, for example, a transition of a degree of sclerosis of an atrioventricular valve or a semilunar valve, or a transition of a systolic function or a diastolic function of a ventricle or an atrium based on the changes over time of the frequency with peak power.

In the medical device according to the present invention, the frequency analysis unit preferably analyzes a heart sound frequency to identify a sound at least in a rapid filling phase. In this application, the "rapid filling phase" means a period from 7.2/H (sec) after the second heart sound of the heart sound to 12.0/H (sec). In this application, the variable H indicates a heart rate (bpm) of the subject. For example, when the heart rate is 60, 7.2/H (sec) later means 0.12 (sec) later, that is, 120 ms later. Since there is the individual difference in the rapid filling phase, the period corresponding to the heart rate H of the subject is used. Since the ventricle is relaxed and the ventricular pressure becomes lower than the atrial pressure in the rapid filling phase, the valve leaflet opens and the blood in the atrium flows into the ventricle. At this time, when the ventricle is rapidly filled with blood, the vibration of the ventricle is recorded as a sound. In this case, the frequency analysis unit may trace changes over time of a frequency with peak power in a frequency band in the rapid filling phase. A cardiac function diagnostic unit is preferably configured to identify a transition of a severity of heart disease or heart failure based on the changes over time of the frequency with peak power of the sound in the rapid filling phase.

In the medical device according to the present invention, the frequency analysis unit may analyze the heart sound frequency to identify a first heart sound and a second heart sound, and identify the frequency with peak power in the frequency band for each of the first heart sound and the second heart sound. Alternatively, the frequency analysis unit may analyze the heart sound frequency to identify sounds of a systole and a diastole of the heart, and identify the frequency with peak power for each sound of the systole and the diastole. In this case, the cardiac function diagnostic unit may be configured to identify a degree of sclerosis of an atrioventricular valve or a semilunar valve, or a systolic function or a diastolic function of a ventricle or an atrium based on the frequency with peak power. The first heart sound is a low-pitched sound generated when the atrioventricular valve is closed after the end of atrial systole. When the atrioventricular valve is closed, ventricular systole starts, the ventricular pressure becomes higher than the intra-arterial pressure, and the arterial valve is opened and ejected. The second heart sound is a high-pitched sound generated when the intra-arterial pressure becomes higher than the ventricular pressure and the arterial valve is closed after the end of the ejection. The above-described rapid filling phase (also referred to as a heart sound diastolic period) is present after the second heart sound, and sounds are generated in the period in some cases.

The medical device according to the present invention may further include an electrocardiograph. In this case, the frequency analysis unit may identify at least the first heart sound and the second heart sound or identify the sounds of a systole and a diastole based on the heart sound frequency obtained from the vibration receiver and electrocardiogram information obtained from the electrocardiograph.

In the medical device according to the present invention, when the frequency analysis unit identifies a frequency with peak power based on the sound in the rapid filling phase of the heart sound, the cardiac function diagnostic unit may be configured to identify whether an onset of heart disease or heart failure is present or not based on the frequency with peak power of the sound in the rapid filling phase.

The second aspect of the present invention relates to a computer program. The computer program according to the present invention causes a computer to execute a process of identifying a frequency with peak power among heart sounds in a frequency band including less than 20 Hz collected by a vibration receiver.

Advantageous Effects of the Invention

The medical device according to the present invention allows obtaining the measurement result with high reproducibility even when the strength or the position of applying the vibration receiver to the examination site is not constant.

DESCRIPTION OF PREFERRED EMBODIMENTS

The following describes an embodiment of the present invention using the drawings. The present invention is not limited to the embodiment described below and includes ones appropriately changed in an obvious range by those skilled in the art from the following embodiment.

Figure 1:
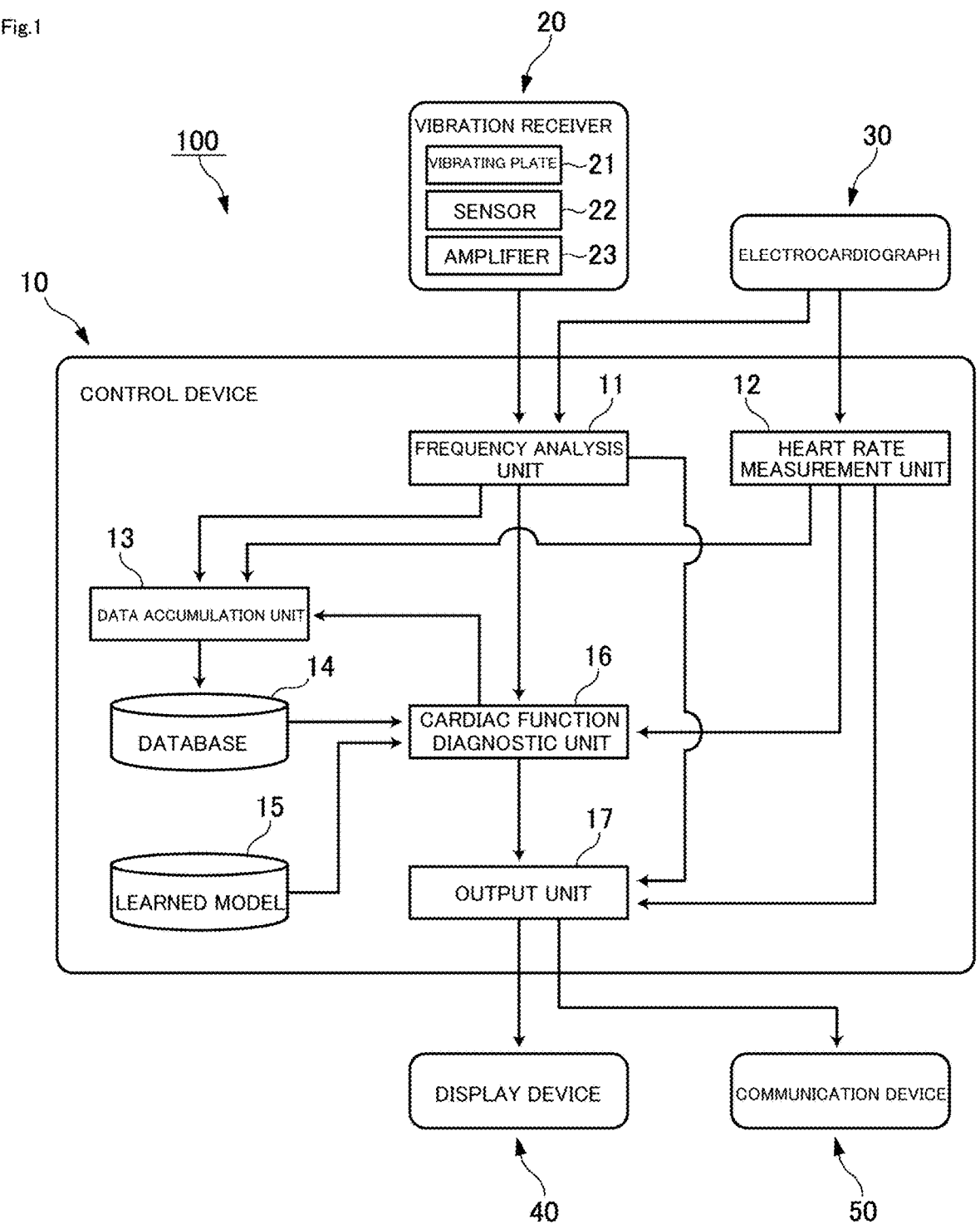
FIG. 1 is a block diagram conceptually illustrating a function composition of a medical device according to the present invention.

FIG. 1 illustrates the overall configuration of a medical device 100 (specifically, cardiac function diagnostic device) according to the present invention. As illustrated in FIG. 1, the medical device 100 includes a control device 10, a vibration receiver 20, an electrocardiograph 30, a display device 40, and a communication device 50. The control device 10 is achievable by a computer that stores a specific program. For example, the control device 10 may be a mobile terminal such as a laptop computer, a tablet computer, and a smart phone, or may be a stationary terminal such as a desktop computer and a web server. When a predetermined signal is input from the vibration receiver 20 and the electrocardiograph 30, the control device 10 performs an arithmetic operation in accordance with the program and outputs the result of the arithmetic operation to the display device 40 and the communication device 50.

FIG. 1 also illustrates function blocks of the control device 10 achieved by the program specific to the present invention. As illustrated in FIG. 1, the control device 10 includes a frequency analysis unit 11, a heart rate measurement unit 12, a data accumulation unit 13, a database 14, a learned model 15, a cardiac function diagnostic unit 16, and an output unit 17. That is, the program is described to cause the computer to achieve these functions.

In the present invention, as the vibration receiver 20, one configured to appropriately collected a heart sound of a subject down to a non-audible low frequency band of less than 20 Hz (0 to 20 Hz) (for example, electronic stethoscope) is used. The vibration receiver 20 includes, for example, a vibrating plate 21 directly touched with the skin of the subject, a sensor 22 configured to sense a vibration (sound) of the vibrating plate 21, and an amplifier 33 configured to amplify the signal sensed by the sensor 22.

The vibrating plate 21 preferably includes a material with frequency characteristic allowing transmitting the non-audible low frequency band of less than 20 Hz. The material constituting the vibrating plate 21 is not specifically limited insofar as the material can transmit the vibration of less than 20 Hz. An exemplary material of the vibrating plate 21 suitable for a medical treatment includes a silicon rubber. As a hardness of the silicon rubber, one having 30 to 80, or 30 to 40 (measured by type A durometer in accordance with Japanese Industrial Standard K 6253) is preferred to be used.

As the sensor 22, one configured to sense the heart sound including the non-audible low frequency band of less than 20 Hz is employed. Specifically, a piezoelectric sensor is preferred to be used as the sensor 22. The piezoelectric sensor directly senses the vibration of the vibrating plate 21, and converts a force (vibration) applied to the vibrating plate 21 into a voltage signal by a piezoelectric effect. The piezoelectric sensor basically includes a piezoelectric element and a plurality of electrodes sandwiching the piezoelectric element. While a common electronic stethoscope often employs a dynamic microphone or a condenser microphone, since these microphones are configured to sense a vibration of air as a sound, the frequency band of less than 20 Hz possibly fails to be appropriately sensed. Therefore, the piezoelectric sensor configured to appropriately collect the sound in such low range is preferred to be used.

An amplifier 23 is a circuit for amplifying a signal obtained by the sensor 22. The amplifier 23 amplifies a voltage signal obtained by the sensor 22 (specifically, piezoelectric sensor). The amplifier 23 only needs to have a performance allowing amplification of the frequency band including the band of less than 20 Hz.

As described above, the vibration receiver 20 can obtain biological vibration information (heart sound information) digitized including up to the target frequency range by sensing by the sensor 22 (for example, piezoelectric sensor) configured to sense the frequency band of less than 20 Hz and amplifying the signal obtained by the sensor 22 by the amplifier 23 configured to amplify even less than 20 Hz via the vibrating plate 21 including the material with the frequency characteristic allowing transmitting even the non-audible low frequency band. The biological vibration information obtained by the vibration receiver 20 is input to the control device 10.

The electrocardiograph 30 measures an electrocardiogram recording a flow of electricity inside the heart of the subject. As the electrocardiograph 30, a publicly known one is usable, and a plurality of electrodes and an electrocardiogram processing circuit are generally included. An electrocardiogram signal measured by the electrocardiograph 30 is input to the control device 10.

Figure 2:
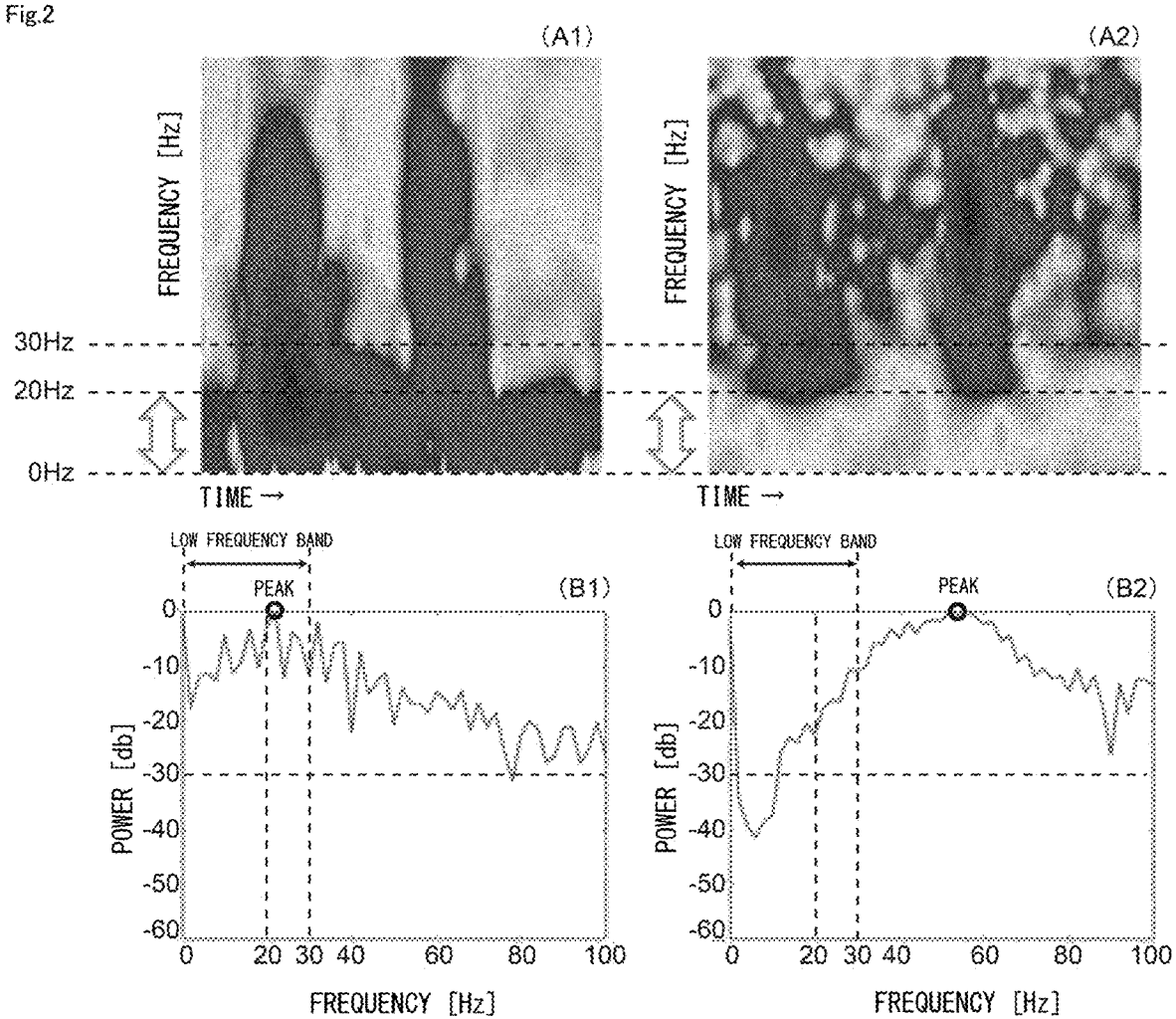
FIG. 2 illustrates three-dimensional data (A1, A2) and two-dimensional data (B1, B2) indicating frequency characteristics of collected heart sounds for a vibration receiver configured to collect sounds down to a non-audible low frequency band of less than 20 Hz and a common electronic device having a purpose of collecting sounds of an audible range of mainly 20 Hz or more in comparison.

The frequency analysis unit 11 of the control device 10 performs a process of analyzing the heart sound information obtained from the vibration receiver 20 and specifying the frequency with peak power [db] (amplitude) in the heart sound frequency band including the non-audible frequency band of less than 20 Hz. Specifically, A1 and B1 of FIG. 2 are graphs illustrating the results of measuring the frequency characteristic in one beat of the heart sound of a normal subject using the vibration receiver 20 configured to collect the sound down to the non-audible low frequency band. That is, the frequency with peak power is a frequency with largest sound volume. A1 of FIG. 2 is a spectrogram (three-dimensional graph) illustrating changes over time of the sound volume at each frequency for one beat of the heart sound. In the spectrogram, for example, the vertical axis indicates the frequency, the horizontal axis indicates a time, and the power is indicated by color tones or brightness in the graph (vertical axis and horizontal axis are interchangeable). While FIG. 2 is illustrated in black and white, actually, the frequency band with large power is illustrated by red, and the frequency band with the small power is illustrated in blue. B1 of FIG. 2 is a two-dimensional graph illustrating the magnitude of the power (amplitude) for each frequency for one beat of the heart sound. In this two-dimensional graph, a difference from the peak power is indicated by −db assuming the peak power as a reference (zero).

As illustrated in B1 of FIG. 2, it is seen that when the heart sound of the subject is measured using the vibration receiver 20 configured to appropriately collect the sound of the non-audible frequency band of less than 20 Hz, the frequency with peak power is around 20 Hz (10 to 30 Hz) in the frequency band of the entire heart sound. In other words, the frequency component of the peak power appears in the low frequency band of 30 Hz or less. Additionally, it is seen that the heart sound has the amplitude with the power relatively increased in the low frequency band of 30 Hz or less. That is, every power in the low frequency band of 30 Hz or less falls within −30 db compared with the peak power. More specifically, it can be said that every power in the low frequency band of 30 Hz or less falls within −25 db or within −20 db compared with the peak power. In contrast, in the frequency band exceeding 30 Hz, the frequency component not falling within −30 db, the frequency component not falling within −25 db, and the frequency component not falling within −20 db compared with the peak power are included. Thus, it is seen that the heart sound is originally a sound with a relatively large power in the low frequency band of 0 to 30 Hz, more specifically, the non-audible low frequency band of 0 to 20 Hz. Therefore, as proposed in the present invention, it can be said that, as the vibration receiver 20, one configured to appropriately collected the sound in the non-audible frequency band of less than 20 Hz of the heart sound is preferred to be employed.

In contrast, A2 and B2 of FIG. 2 illustrate the frequency characteristic of the heart sound of the normal subject (the same person as A1, B1) measured using a common electronic stethoscope (specifically, a condenser microphone is included). As illustrated in A2 of FIG. 2, the common electronic stethoscope does not have the performance allowing appropriately collecting the sound in the non-audible low frequency band of less than 20 Hz, and it is seen that the power is evenly low in the band of less than 20 Hz. In B2 of FIG. 2, compared with B1, it is seen that the sound is not appropriately collected in the band of less than 20 Hz and the power is low in this band. Thus, as a result of excluding the band around 20 Hz (0 to 30 Hz) from the main target of collecting the sound, the use of the common stethoscope causes the peak power of the heart sound to appear in the frequency band around 60 Hz. Here, as illustrated in the graph of B1 in FIG. 2, it is seen that when the sound is appropriately collected down to the non-audible low frequency band, the heart sound originally has the power obviously large in the band around 20 Hz compared with the power in the band around 60 Hz. The larger the power is, the more reduced the influence by the strength and the position of applying the stethoscope to the examination site. Accordingly, as the present invention, with the configuration for identifying the frequency with peak power appeared around 20 Hz, the measurement result highly reproducible compared with the common stethoscope can be obtained.

The frequency analysis unit 11 may be configured to quantify (numerically express) the value of the peak power of the heart sound collected by the vibration receiver 20. In the example illustrated in FIG. 2, while the peak power is assumed to the reference (zero) and the other powers are relatively indicated in the comparison with it, the frequency analysis unit 11 can calculate the value of the peak power as an absolute numerical value. The frequency analysis unit 11 can also trace the changes over time of the frequency of the peak power. For example, even when the frequency around 20 Hz indicates the peak power at the healthy state of the subject, the frequency indicating the peak power changes to the proximity of 10 Hz or the proximity of 30 Hz in some cases when the state of the cardiac function changes even for the same subject. Therefore, by tracing the changes over time of the frequency indicating the peak power, at least a sign of the change in the cardiac function of the subject can be found.

The heart sound is a sound generated in accordance with the heartbeat, and a first heart sound and a second heart sound are generated. In these sounds, the sound generated immediately after the start of a systole is the first heart sound, and the sound generated at the border between a systole and a diastole is the second heart sound. A rapid filling phase is present after the second heart sound. The rapid filling phase is a period from 7.2/H (sec) after the second heart sound to 12.0/H (sec). A sound is generated in this rapid filling phase in some cases. As described above, H is the heart rate of the subject. The above-described sound is referred to as a heart murmur or an extra heart sound in some cases. While the sound in the rapid filling phase is generated in accordance with the heartbeat, it is a sound not generated in a normal heart. In the frequency analysis unit 11, it is preferred that for example, by generating the spectrogram illustrated in A1 of FIG. 2 or another two-dimensional graph and analyzing the changes over time of the heart sound frequency, the first heart sound and the second heart sound of the heart sound, or the sound generated in the subsequent rapid filling phase is identified. The frequency analysis unit 11 can identify a sound of the systole and a sound of the diastole instead of identifying the first heart sound and the second heart sound. When the first heart sound, the second heart sound, and the rapid filling phase are identified, the frequency analysis unit 11 may identify the frequencies with peak power for the respective sound components.

The frequency analysis unit 11 may identify the first heart sound and the second heart sound, or the sound generated in the subsequent rapid filling phase based on electrocardiogram information obtained from the electrocardiograph 30 in addition to or instead of the heart sound frequencies obtained from the vibration receiver 20. The frequency analysis unit 11 can identify the sound of the systole and the sound of the diastole instead of identifying the first heart sound and the second heart sound using the electrocardiogram information. Thus, by the use of the electrocardiogram information, the frequency analysis unit 11 can more accurately identify the sound components of the heart sounds such as the first heart sound, the second heart sound, and the sound in the rapid filling phase.

The heart rate measurement unit 13 measures the heart rate of the subject based on the electrocardiogram information obtained from the electrocardiograph 30. For example, the heart rate measurement unit 13 can obtain the heart rate by counting periodicity of the strength and weakness of the sound component included in the electrocardiogram information for a certain period. While the heart rate measurement unit 13 measures the heart rate based on the electrocardiogram information input from the electrocardiograph 30 in the example illustrated in FIG. 1, for example, it is allowed that the vibration receiver 20 is applied to the chest of the subject for a certain period and the heart rate is measured based on the heart sound information obtained from the vibration receiver 20.

The data accumulation unit 13 stores the analysis result (frequency value of peak power, its changes over time, and the like) by the frequency analysis unit 11 and heart rate data measured by the heart rate measurement unit 13 in the database 14. Especially, at the beginning of a medical examination, since the heart sound and the electrocardiogram of the subject are obtained at the same time or under the same condition, it is preferred that the value of the frequency with peak power obtained from those heart sounds and the heart rate obtained from the electrocardiogram are mutually associated and stored as one data set in the database. A plurality of the data sets may be generated for one subject. Even when the data set as described above is not generated, it is appropriate that the data accumulation unit 13 stores the value of the frequency with peak power and the value of the heart rate in the database 14 as needed when they are obtained. Thus, the data accumulation unit 13 is configured to accumulate various kinds of biometric data obtained by the frequency analysis unit 11 and the heart rate measurement unit 12 in the database 14 as necessary.

The learned model 15 is model data in which parameters (what is called "weights") are adjusted through a machine learning on biometric data of a large number of subjects. For example, the machine learning such as deep learning is performed with the data set of the value of the frequency with peak power in the heart sound and the parameter representing the state of the cardiac function (for example, degree of severity of cardiac dysfunction) as teaching data for a large number of subjects, thus generating the learned model 15. In this case, the heart sound of one subject is analyzed to identify the value of the frequency with peak power, and the learned model 15 is referred while having the frequency value as an input value, thereby obtaining the parameter representing the state of the cardiac function as an output value corresponding to the input value. The medical device 100 according to the present invention may be configured to preliminarily include such learned model 15.

The cardiac function diagnostic unit 16 has a function of diagnosing the cardiac function of the subject based on the analysis result by the frequency analysis unit 11. For example, the cardiac function diagnostic unit 16 diagnoses the severity of a specific disease and its transition based on the frequency value with peak power of the heart sound identified by the frequency analysis unit 11 and its changes over time. Specifically, the cardiac function diagnostic unit 16 may determine the onset of a specific disease when the frequency value with peak power of the heart sound exceeds a certain threshold, or may identify the transition of a specific disease based on the degree of change of the frequency value with peak power. The cardiac function diagnostic unit 16 can perform the diagnosis process as described above according to a preliminarily described program, or may refer to the learned model 15 having the frequency value with peak power of the heart sound as the input and obtain the diagnostic result as the output.

Figure 3:
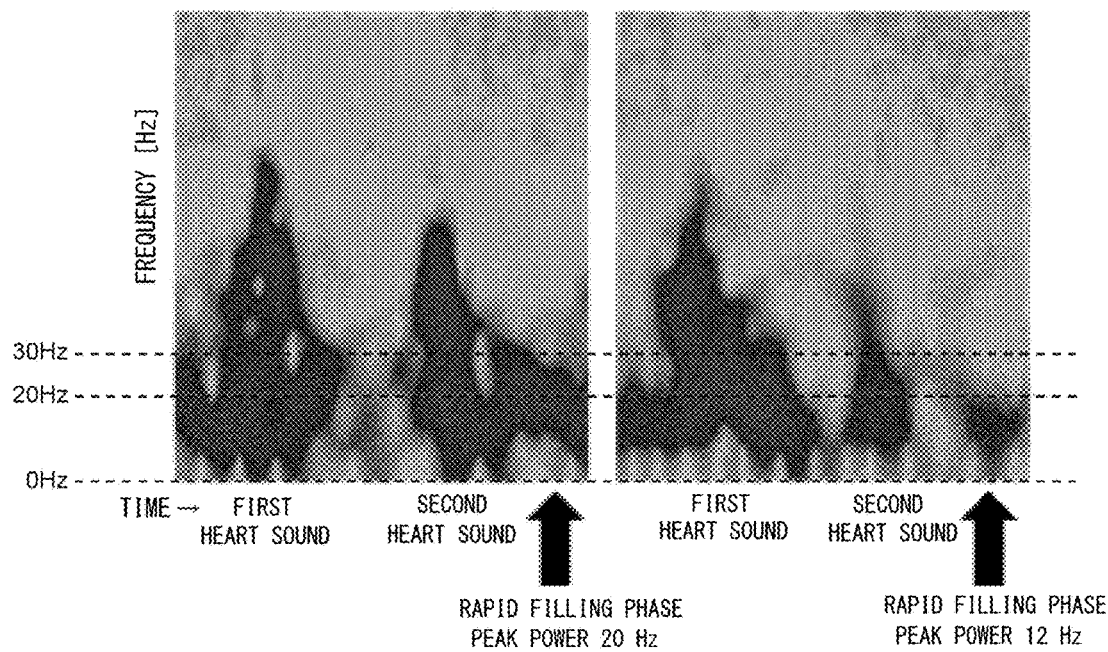
FIG. 3 illustrates a result of measuring heart sounds of an identical person by an electronic stethoscope configured to collect the sounds down to the non-audible low frequency band, and the results of a poor control and a good control of heart failure are compared in FIG. 3.

Here, with reference to FIG. 3, an exemplary diagnosis process by the cardiac function diagnostic unit 16 will be described. In FIG. 3, for the identical subject, a spectrogram illustrating the frequency characteristic of the heart sound in a poor control of heart failure and a spectrogram illustrating the frequency characteristic of the heart sound in a good control of heart failure are illustrated side by side. First, the frequency analysis unit 11 performs a frequency analysis of the heart sound of the subject, thereby identifying the sound components in the rapid filling phase, identifying the frequency with peak power in the frequency band of the sound components in the rapid filling phase, and quantifying it. In the example illustrated in FIG. 3, the peak power of the sound in the rapid filling phase under the poor control is identified as 20 Hz, the peak power of the sound in the rapid filling phase under the good control is identified as 12 Hz. Therefore, tracing the peak power of the heart sound in the rapid filling phase allows identifying whether the control of heart failure is good or not. Especially, for this subject, while there is no problem when the peak power of the sound in the rapid filling phase is around 12 Hz, the state of heart failure can be determined as the poor control at the proximity of 20 Hz. Thus, by identifying the peak power of the heart sound in the rapid filling phase of the subject, whether the heart failure (or other heart diseases) has appeared or not can be identified. Furthermore, for this subject, it can be determined that the severity of the heart failure increases as the power of the sound in the rapid filling phase increases from 12 Hz. Therefore, by tracing the changes over time in the frequency value with peak power of the heart sound of the subject in the rapid filling phase, the transition of the severity of the heart failure (or other heart diseases) can be identified. The cardiac function diagnostic unit 16 only needs to output whether the control of the heart failure is good or not and the changes of its severity as the diagnostic result based on the value of the peak power of the sound in the rapid filling phase and its changes over time as described above. The diagnostic result by the cardiac function diagnostic unit 16 is recorded in the database 14 by the data accumulation unit 13. It is appropriate that the frequency values with peak power of the sound in the rapid filling phase under the good control and the poor control are recorded in the database 14 for each subject. Accordingly, the cardiac function diagnostic unit 16 can identify the presence/absence of the heart failure or the heart disease and the transition of its severity based on the information recorded in the database 14 for each subject.

From the analysis result at the timing of the beginning of a systole (first heart sound), the degree of sclerosis of an atrioventricular valve can be identified. From the analysis result at the timing of the end of the systole (second heart sound), the degree of sclerosis of a semilunar valve can be identified. Furthermore, from the analysis result of the low frequency band (30 Hz or less) of the sound collected in the rapid filling phase (period from 7.2/heart rate (sec) after the second heart sound to 12.0/H (sec)), the reduced ventricular diastolic function and the reduction in diastolic compliance can be identified. From the analysis result of the low frequency band (30 Hz or less) of the sound collected in the late diastole (period immediately before the first heart sound from −8.4/H (sec) before to −14.4/H (sec) before P wave), the systolic function of left atrial and the elevation of ventricular end-diastolic pressure can be identified.

The output unit 17 outputs the various information obtained by the frequency analysis unit 11, the heart rate measurement unit 12, or the cardiac function diagnostic unit 16 to the display device 40 and the communication device 50. For example, the output unit 17 can cause the display device 40 to display the graph illustrating the heart sound frequency (two-dimensional or three-dimensional graph illustrated in FIG. 2 and the like), the frequency value of the peak power included in the heart sound, the heart rate, the diagnostic result of the cardiac function, and the like. The output unit 17 can also transmit the various information obtained by the frequency analysis unit 11, the heart rate measurement unit 12, or the cardiac function diagnostic unit 16 to an external terminal via the communication device 50 through an information communication network such as Internet. For example, it is preferred that the subject himself/herself operates the medical device 100 according to the present invention to measure body information of himself/herself, and transmits the body information to a terminal of a doctor located in a remote area. Accordingly, the subject can receive a remote medical service using the medical device 100 of the present invention.

Next, criteria for identifying presence/absence of various kinds of diseases by the cardiac function diagnostic unit 16 will be described with specific examples.

Figure 4:
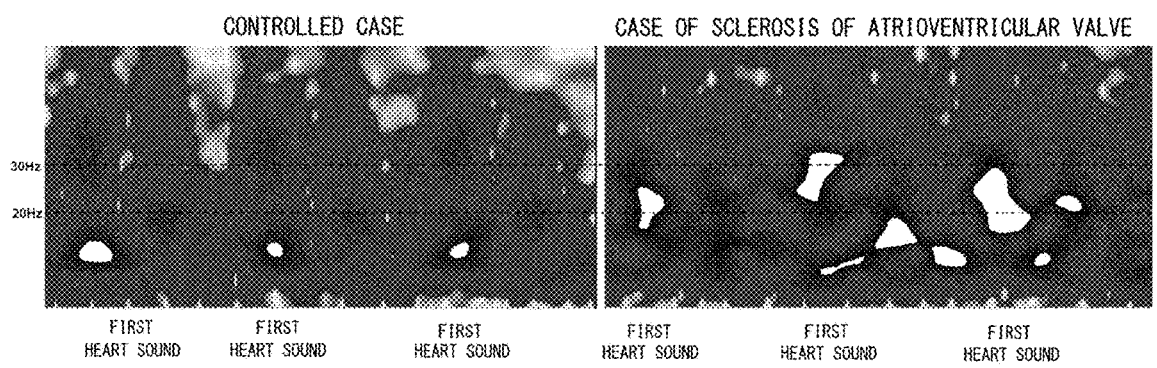
FIG. 4 illustrates spectrograms of heart sounds in a case of sclerosis of an atrioventricular valve and its controlled (good) case.

FIG. 4 illustrates spectrograms of heart sounds in a case of sclerosis of an atrioventricular valve and its controlled (good) case. In the controlled case, the peak power is recognized at constant positions in the low frequency band of 20 Hz or less in the first heart sound region. In contrast, in the case of the sclerosis of an atrioventricular valve, it is recognized that the frequency band in which the peak power is present is wide and unstable, and appears also at 20 Hz or more or 30 Hz or more. Therefore, by confirming whether the frequency band with peak power appears at the constant positions in the first heart sound region and confirming the value of the frequency band with peak power, the presence/absence of the sclerosis of an atrioventricular valve can be identified.

Figure 5:
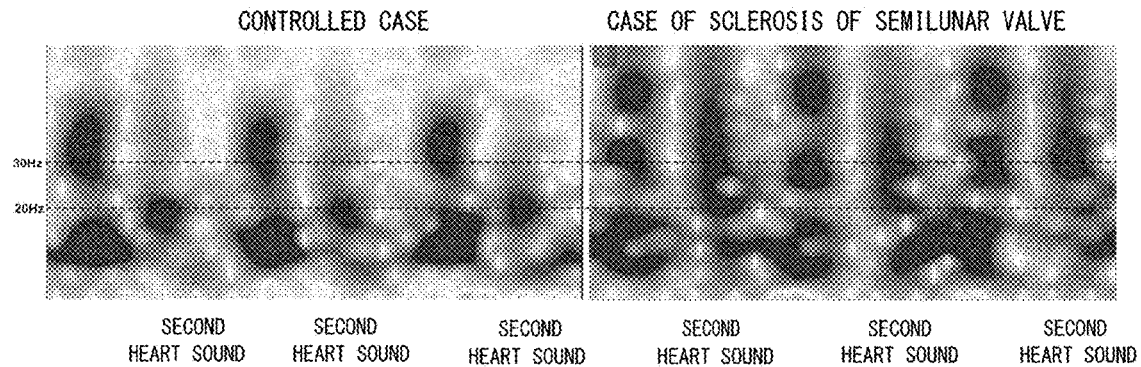
FIG. 5 illustrates spectrograms of heart sounds in a case of sclerosis of a semilunar valve and its controlled (good) case.

FIG. 5 illustrates spectrograms of heart sounds in a case of sclerosis of a semilunar valve and its controlled (good) case. In the controlled case, the peak power is recognized at constant positions in the low frequency band around 20 Hz in the second heart sound region. In contrast, in the case of the sclerosis of a semilunar valve, it is recognized that the frequency band with peak power is higher. In the case of the sclerosis of a semilunar valve, a signal extending in the direction of the time axis appears in the low frequency band of 20 Hz or less, and the instability is confirmed. Therefore, by confirming whether the frequency with peak power is around 20 Hz and confirming whether it appears as a stable signal at the constant positions, the presence/absence of the sclerosis of a semilunar valve can be identified.

Figure 6:
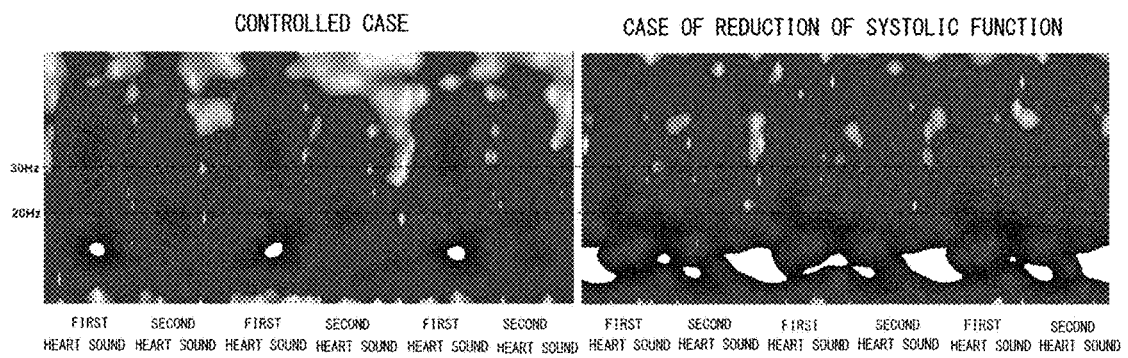
FIG. 6 illustrates spectrograms of heart sounds in a case of reduction of systolic function and its controlled (good) case.

FIG. 6 illustrates spectrograms of heart sounds in a case of reduction of systolic function and its controlled (good) case. In the controlled case, in the rapid filling phase (period from 7.2/H (sec) after the second heart sound to 12.0/H (sec)), no signal is recognized in the low frequency band of 20 Hz or less. In contrast, in the case of the reduction of systolic function, the signals with large power are recognized in the low frequency band of 20 Hz or less. In the first heart sound region, while the frequency with peak power is stably present in the low frequency band of 20 Hz or less in the controlled case, the frequency band in which the peak power is present is unstable in the case of the reduction of systolic function. Therefore, by confirming whether the frequency with peak power of 20 Hz or less appears at the constant positions and confirming whether the frequency with peak power of 20 Hz or less appears in the rapid filling phase, the presence/absence of the reduction of systolic function can be identified.

Figure 7:
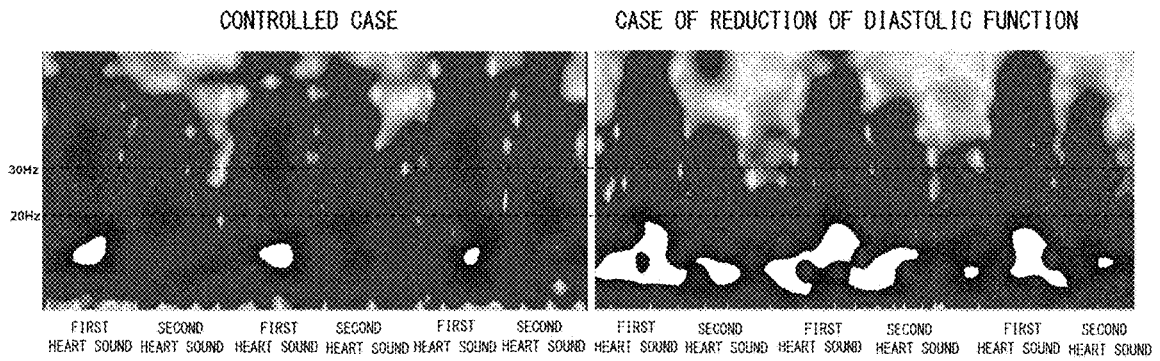
FIG. 7 illustrates spectrograms of heart sounds in a case of reduction of diastolic function and its controlled (good) case.

FIG. 7 illustrates spectrograms of heart sounds in a case of reduction of diastolic function and its controlled (good) case. In the controlled case, in the rapid filling phase (period from 7.2/H (sec) after the second heart sound to 12.0/H (sec)), no signal is recognized in the low frequency band of 20 Hz or less. In contrast, in the case of the reduction of diastolic function, the signals with large power are recognized in the low frequency band of 20 Hz or less. Therefore, by confirming whether the frequency with peak power of 20 Hz or less appears at the constant positions and confirming whether the frequency with peak power of 20 Hz or less appears in the rapid filling phase, the presence/absence of the reduction of diastolic function can be identified.

Figure 8:
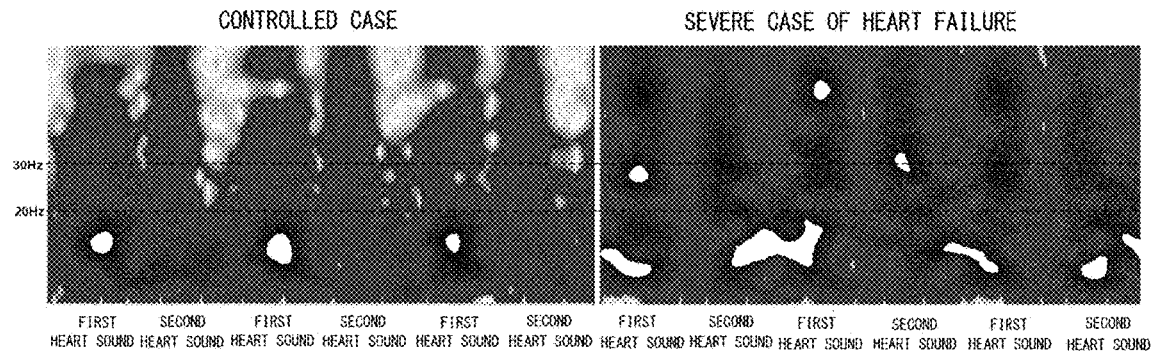
FIG. 8 illustrates spectrograms of heart sounds in a severe case of heart failure and its controlled (good) case.

FIG. 8 illustrates spectrograms of heart sounds in a severe case of heart failure and its controlled (good) case. In the controlled case, the frequency with peak power is present at constant positions (first heart sound regions) in the low frequency band of 20 Hz or less. In contrast, in the severe case of heart failure, the frequency with large power can be recognized in the region of 20 Hz or less in the rapid filling phase (period from 7.2/H (sec) after the second heart sound to 12.0/H (sec)). Therefore, by confirming whether the frequency with peak power of 20 Hz or less appears at the constant positions and confirming whether the frequency with peak power appears in the region of 20 Hz or less in the rapid filling phase, the severity of heart failure can be identified.

Figure 9:
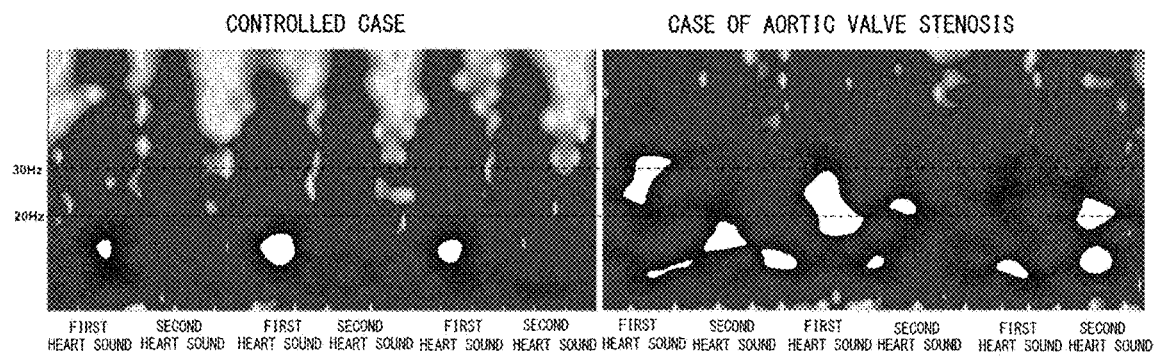
FIG. 9 illustrates spectrograms of heart sounds in a case of aortic valve stenosis and its controlled (good) case.

FIG. 9 illustrates spectrograms of heart sounds in a case of aortic valve stenosis and its controlled (good) case. In the controlled case, the frequency with peak power is present at constant positions (first heart sound regions) in the low frequency band of 20 Hz or less. In contrast, in the case of aortic valve stenosis, the frequency band with peak power of 20 Hz or less is not recognized in the first heart sound regions, and unstable signals are recognized from the beginning of systole to the end of the systole. In the case of aortic valve stenosis, the value of the frequency with large power was recognized in the region of 20 Hz or less in the rapid filling phase (period from 7.2/H (sec) after the second heart sound to 12.0/H (sec)). Therefore, by confirming whether the frequency with peak power appears at constant positions in the region of 20 Hz or less from the beginning of systole to the end of the systole, and confirming whether the frequency with peak power appears in the region of 20 Hz or less in the rapid filling phase, the aortic valve stenosis can be identified.

Figure 10:
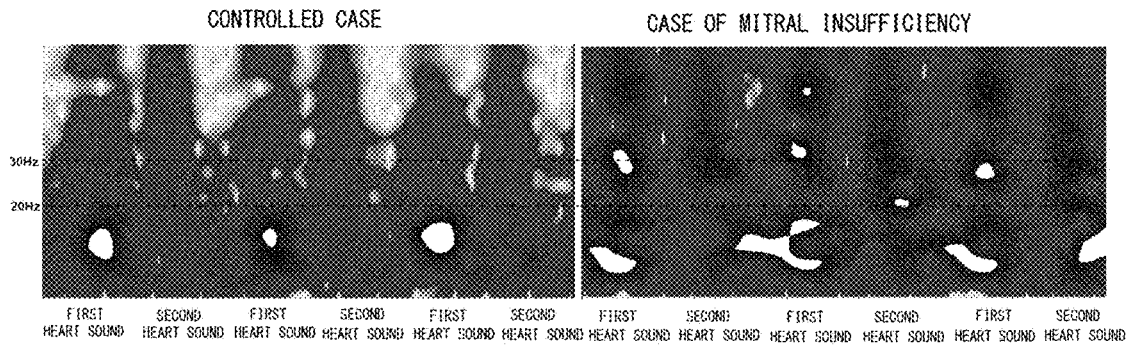
FIG. 10 illustrates spectrograms of heart sounds in a case of mitral insufficiency and its controlled (good) case.

FIG. 10 illustrates spectrograms of heart sounds in a case of mitral insufficiency and its controlled (good) case. In the controlled case, the signals with large power constantly appear in the low frequency band of 20 Hz or less in the first heart sound regions. The frequency with peak power is present at constant positions (first heart sound regions) in the low frequency band of 20 Hz or less. In contrast in the case of mitral insufficiency, the signals with large power are recognized in the low frequency band of 20 Hz or more in the first heart sound regions. The frequencies with large power were recognized in the region of 20 Hz or less in the rapid filling phase (period from 7.2/H (sec) after the second heart sound to 12.0/H (sec)). Therefore, by confirming whether the frequency value with large power in the first heart sound region is a low frequency value of 20 Hz or more, confirming whether the frequency with peak power of 20 Hz or less appears at constant positions, and confirming whether the frequency with peak power of 20 Hz or less appears in the rapid filling phase, the mitral insufficiency can be identified.

In this application, the embodiments of the present invention have been described above by referring to the drawings to express the contents of the present invention. However, the present invention is not limited to the embodiments described above, but includes changed configurations and improved configurations obvious to those skilled in the art based on the matters described in this application.

DESCRIPTION OF REFERENCE SIGNS

10 . . . control device
11 . . . frequency analysis unit
12 . . . heart rate measurement unit
13 . . . data accumulation unit
14 . . . database
15 . . . learned model
16 . . . cardiac function diagnostic unit
17 . . . output unit
20 . . . vibration receiver
21 . . . vibrating plate
22 . . . sensor
23 . . . amplifier
40 . . . display device
50 . . . communication device
100 . . . medical device (cardiac function diagnostic device)

The invention claimed is:

1. A medical device comprising:
a vibrating receiver configured to collect heart sounds in a frequency band at least from 0 to 20 Hz, wherein the vibration receiver comprises
a vibrating plate made of silicone rubber having a hardness of 30 to 80 durometer,
a piezoelectric sensor configured to directly sense vibration of the vibrating plate and convert the sensed vibration into electrical signals, and
an amplifier configured to amplify the electrical signals; and
a computer, wherein the computer is configured to:
identify a frequency with peak power in the frequency band; and
diagnose cardiac function based on the changes over time of the frequency with peak power.

2. The medical device according to claim 1, wherein the computer is configured to identify the frequency with peak power in the frequency band at least from 0 to 20 Hz.

3. The medical device according to claim 1, wherein the computer is configured to trace changes over time of the frequency with peak power.

4. The medical device according to claim 3, wherein the computer is configured to identify a transition of a degree of sclerosis of an atrioventricular valve or a semilunar valve, or a transition of a systolic function or a diastolic function of a ventricle or an atrium based on the changes over time of the frequency with peak power.

5. The medical device according to claim 3, wherein the computer is configured to analyze a heart sound frequency to identify a sound at least in a rapid filling phase (a period from 7.2/H (sec) after the second heart sound to 12.0/H (sec), H indicates a heart rate here) and traces changes over time of a frequency with peak power in a frequency band in the rapid filling phase, and
identify a transition of a severity of heart disease or heart failure based on the changes over time of the frequency with peak power of the sound in the rapid filling phase.

6. The medical device according to claim 1, wherein the computer is configured to analyze the heart sound frequency to identify at least a first heart sound and a second heart sound or identify sounds of a systole and a diastole, and identify the frequency with peak power in the frequency band for each of the first heart sound and the second heart sound or identify the frequency with peak power in the frequency band for each sound of the systole and the diastole.

7. The medical device according to claim 6, further comprising
an electrocardiogram, wherein
the computer is configured to identify at least the first heart sound and the second heart sound or identify the sounds of the systole and the diastole based on the heart sound frequency and electrocardiogram information obtained from the electrocardiograph.

8. The medical device according to claim 6, wherein the computer is configured to identify a degree of sclerosis of an atrioventricular valve or a semilunar valve, or a systolic function or a diastolic function of a ventricle or an atrium based on the frequency with peak power.

9. The medical device according to claim 1, wherein the computer is configured to analyze the heart sound frequency to identify a sound at least in a rapid filling phase (a period from 7.2/H (sec) after the second heart sound to 12.0/H (sec), H indicates a heart rate here) and identify a frequency with peak power in the frequency band in the rapid filling phase, and
identify whether an onset of heart disease or heart failure is present or not based on the frequency with peak power of the sound in the rapid filling phase.

* * * * *